United States Patent
Yang

(10) Patent No.: US 12,336,642 B2
(45) Date of Patent: Jun. 24, 2025

(54) BACK SUPPORT SYSTEM FOR LOWER BACK PAIN

(71) Applicant: Demao Yang, Mountain View, CA (US)

(72) Inventor: Demao Yang, Mountain View, CA (US)

( * ) Notice: Subject to any disclaimer, the term of this patent is extended or adjusted under 35 U.S.C. 154(b) by 207 days.

(21) Appl. No.: 16/168,431

(22) Filed: Oct. 23, 2018

(65) Prior Publication Data

US 2020/0121086 A1   Apr. 23, 2020

(51) Int. Cl.
*A47C 7/42* (2006.01)

(52) U.S. Cl.
CPC .................... *A47C 7/425* (2013.01)

(58) Field of Classification Search
CPC .............. A47G 2009/1018; A47G 9/10; A47G 9/1081; A47C 7/425; A47C 7/36; A47C 7/40; A47C 7/405; A47C 7/46; A47C 7/383; A47C 16/005; A47C 20/027; A47C 20/04; A61B 6/04; A61G 13/00; A61G 13/1225; A61G 13/121; A61G 7/07
USPC .... 128/845, 870; 5/633, 634, 636, 637, 639, 5/640, 731, 733, 736
See application file for complete search history.

(56) References Cited

U.S. PATENT DOCUMENTS

| | | | |
|---|---|---|---|
| 3,555,582 A | 1/1971 | Radford | |
| 4,230,099 A | 10/1980 | Richardson | |
| 4,431,232 A | 2/1984 | Hannouche | |
| 4,475,543 A * | 10/1984 | Brooks | A61F 5/028 602/19 |
| 4,502,170 A | 3/1985 | Morrow | |

(Continued)

FOREIGN PATENT DOCUMENTS

| | | |
|---|---|---|
| CN | 2148549 Y | 12/1993 |
| CN | 2314756 Y | 4/1999 |

(Continued)

OTHER PUBLICATIONS

International Search Report from Corresponding PCT Application No. PCT/CN2011/077642, 6 pages, dated Oct. 20, 2011.

(Continued)

*Primary Examiner* — Caitlin A Carreiro
(74) *Attorney, Agent, or Firm* — Christensen, Fonder, Dardi PLLC; Peter S. Dardi

(57) ABSTRACT

A back plate system for recovery of lumbar vertebrae of a human body the system. The system has a plurality of rigid surfaces shaped to place the user's back into a correct posture. A series of the rigid surfaces may be used to gradually bring the user's spine into a correct posture. A first rigid unitary surface has a first concave curve and a first convex curve which reverse direction in a continuous manner. A second rigid unitary surface comprises a second concave curve and a second convex curve which reverse direction in a continuous manner. The height of the second convex curve is greater than the height of the first convex curve. When the series of back plates is used, a user lays on the first rigid unitary surface for a first period of time with the first convex curve under a lumbar region. Then the user lays on the second rigid unitary surface for a second period of time with the second convex curve under the lumbar region.

20 Claims, 10 Drawing Sheets

(56) References Cited

U.S. PATENT DOCUMENTS

| | | | |
|---|---|---|---|
| 4,535,495 A * | 8/1985 | Oldfield | A47C 7/425 297/452.32 |
| 4,796,315 A | 1/1989 | Crew | |
| 4,821,355 A * | 4/1989 | Burkhardt | A47G 9/10 5/636 |
| 5,180,386 A | 1/1993 | Kennedy, Jr. | |
| 5,815,862 A | 10/1998 | Rygiel | |
| 5,893,184 A * | 4/1999 | Murphy | A47C 27/148 297/284.6 |
| 6,360,387 B1 | 3/2002 | Everhart | |
| 6,921,372 B2 | 7/2005 | Shin | |
| 7,536,740 B1 | 5/2009 | Swartz | |
| 8,696,607 B2 | 4/2014 | McDonnell et al. | |
| 2008/0173316 A1 | 7/2008 | Lloyd | |
| 2010/0139000 A1 | 6/2010 | Madeta | |
| 2012/0112506 A1 | 5/2012 | Glyck | |
| 2013/0213407 A1 | 8/2013 | Yang | |
| 2014/0001814 A1 * | 1/2014 | Fujita | B60N 2/64 297/452.48 |
| 2014/0115789 A1 | 5/2014 | Ramdath | |
| 2016/0029822 A1 * | 2/2016 | Cappadona | A47G 9/10 5/636 |
| 2018/0185230 A1 | 7/2018 | Yang | |
| 2018/0200098 A1 | 7/2018 | Swanson | |

FOREIGN PATENT DOCUMENTS

| | | |
|---|---|---|
| CN | 2753231 Y | 1/2006 |
| CN | 201814695 U | 5/2011 |
| EP | 2601914 A1 | 6/2013 |
| JP | 06057325 U | 1/1993 |
| JP | 10117916 | 5/1998 |
| JP | 2013533059 | 8/2013 |
| KR | 020010044318 A | 6/2001 |
| WO | 9308772 | 5/1993 |
| WO | 200200066 | 1/2002 |
| WO | 2009021245 A2 | 2/2009 |

OTHER PUBLICATIONS

Supplementary European Search Report from Corresponding EP Application No. 11814076.3, 6 pages, dated Jun. 24, 2014.

* cited by examiner

BACK SUPPORT SYSTEM FOR LOWER BACK PAIN

FIELD OF THE INVENTION

The field of the invention relates to devices and methods for treating lower back pain.

BACKGROUND OF THE INVENTION

Lower back pain is a common disorder among the population. Multiple factors such as poor long-term posture of the human body, an overload of force, injury, and accidental contusion, contribute to injury and cause pain.

SUMMARY OF THE INVENTION

An embodiment of the invention is a system for recovery of lumbar vertebrae of a human body the system having a first rigid unitary surface and a second rigid unitary surface. The first rigid unitary surface has a first concave curve and a first convex curve which reverse direction in a continuous manner. The second rigid unitary surface comprises a second concave curve and a second convex curve which reverse direction in a continuous manner. The height of the second convex curve is greater than the height of the first convex curve.

When the series of back plates is used, a user lays on the first rigid unitary surface for a first period of time with the first convex curve under a lumbar region. Then the user lays on the second rigid unitary surface for a second period of time with the second convex curve under the lumbar region.

DETAILED DESCRIPTION

Many adults suffer from back pain. Treatment for back pain in a medical facility is expensive, time consuming, and can be drastic. Available home supports either are ineffective or attempt to correct the spinal alignment too quickly, which can make back pain worse in the short term and result in non-compliance in use of the support by a patient. In order to ease a patient into a larger curvature desired for treatment, treatment is provided herein with a series of back support plates that increase in curvature. The surfaces of the back plates are slept on until back pain is reduced before moving to the surface with the next larger curvature. The gradual increase of curvature reduces pain associated with the treatment, increasing the likelihood that a patient will continue treatment and obtain positive results.

Figure 1:
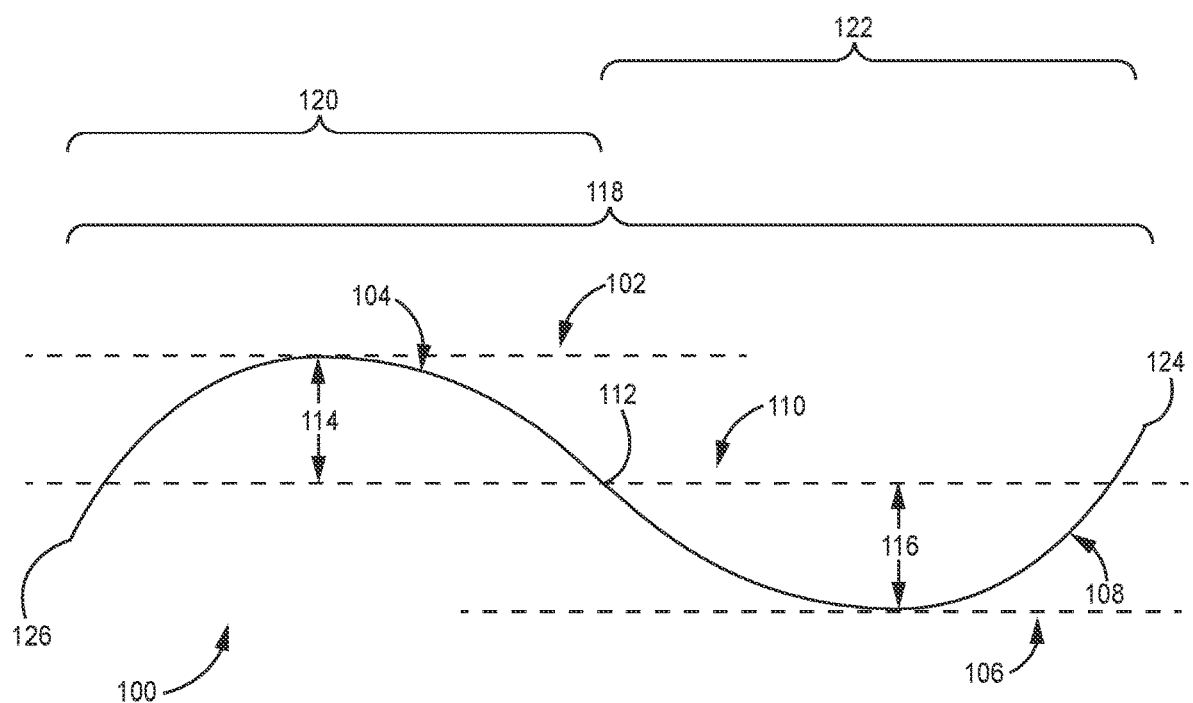
FIG. 1 depicts an s-curve.

FIG. 1 depicts s-curve 100. First tangent line 102 passes through the highest point of convex curve 104. Second tangent line 106 passes through the lowest point of concave curve 108. Midline 110 is parallel to both first and second tangent lines 102, 106. Inflection point 112 is the point at which the s-curve switches from a convex curve to a concave curve. Midline 110 passes through inflection point 112. Height 114 of convex curve 104 is the distance between first tangent line 102 and midline 110. Depth 116 of the concave curve 108 is the distance between second tangent line 106 and midline 110. Length 118 of S-curve 100 is the distance between end 124 of concave curve 108 and end 126 of convex curve 104. Length 120 of convex curve 104 is the distance between end 126 of convex curve 104 and inflection point 112. Length 122 of concave curve 108 is the distance between end 124 of concave curve 108 and inflection point 112.

Figure 2A:
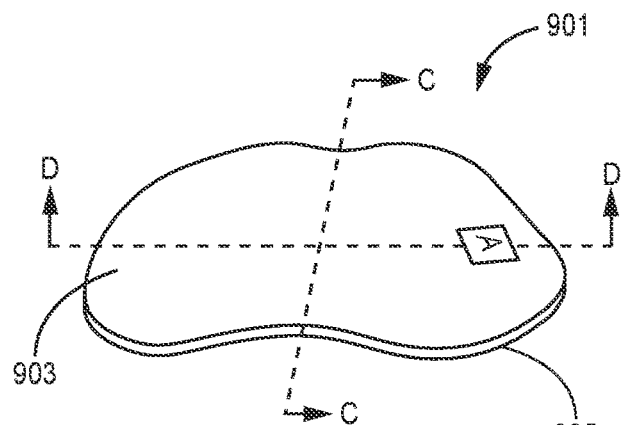
FIG. 2A is a perspective view of a first back plate of a preferred embodiment.
Figure 2B:
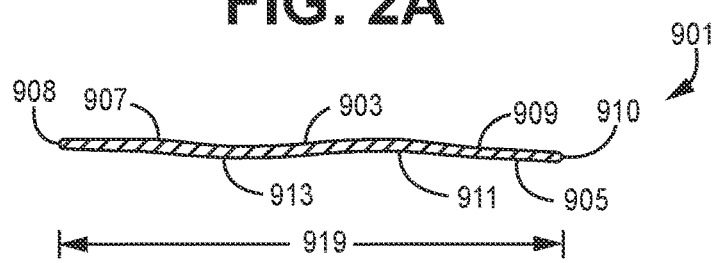
FIG. 2B is a cross-sectional view of the back plate of FIG. 2A taken through line D-D.
Figure 2C:
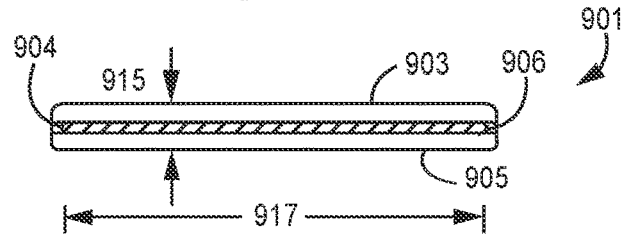
FIG. 2C is a cross-sectional view of the back plate of FIG. 2A taken through line C-C.
Figure 2D:
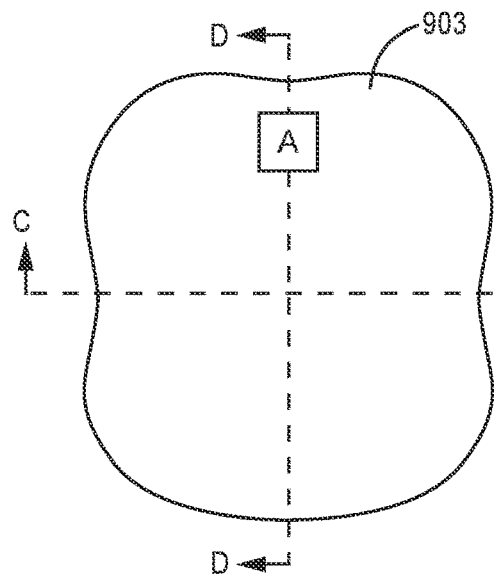
FIG. 2D is a top plane view of the back plate of FIG. 2A.
Figure 2E:
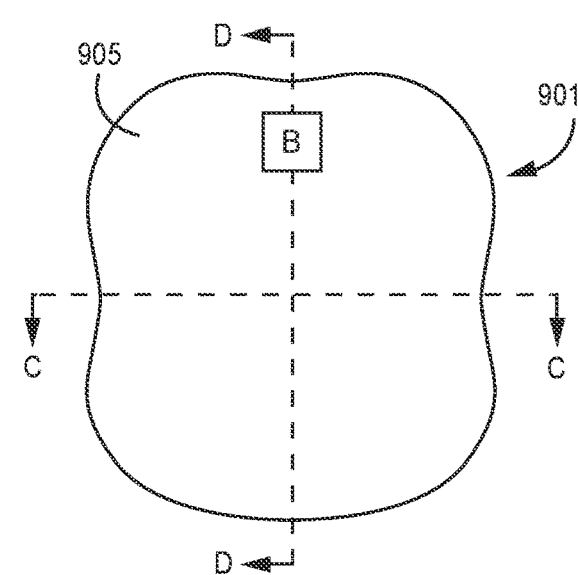
FIG. 2E is a bottom plane view of the back plate of FIG. 2A.
Figure 2F:
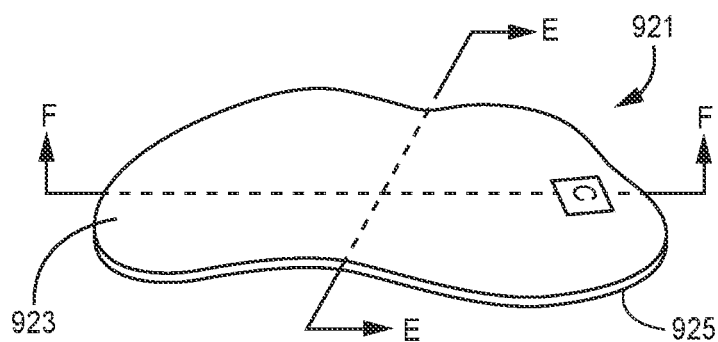
FIG. 2F is a perspective view of the second back plate of the preferred embodiment.
Figure 2G:
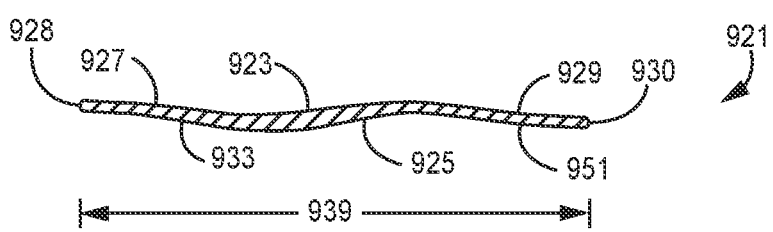
FIG. 2G is a cross-sectional view of the back plate of FIG. 2F taken through line F-F.
Figure 2H:
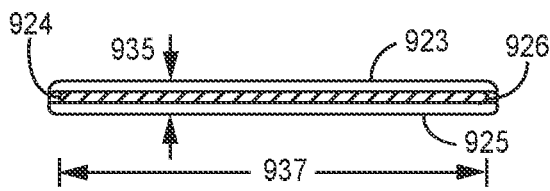
FIG. 2H is a cross-sectional view of the back plate of FIG. 2F taken through line E-E.
Figures 2I, 2J:
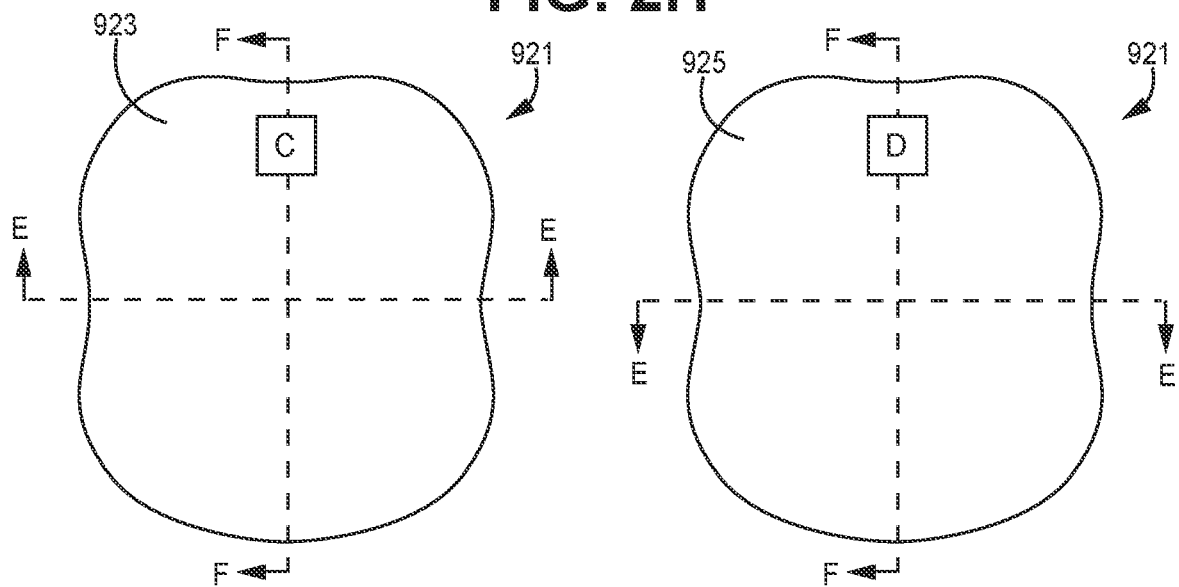
FIG. 2I is a top plane view of the back plate of FIG. 2F.
FIG. 2J is a bottom plane view of the back plate of FIG. 2F.
Figure 3A:
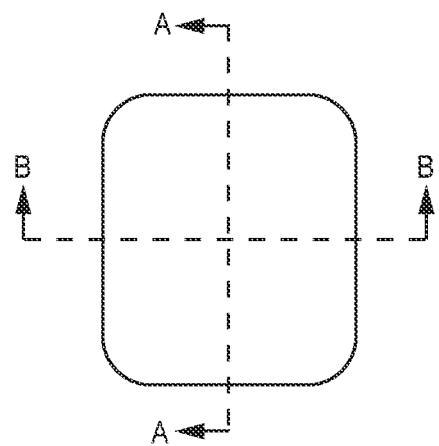
FIGS. 3A-3D depict a top plane view of alternative embodiments of back plates.
Figure 3B:
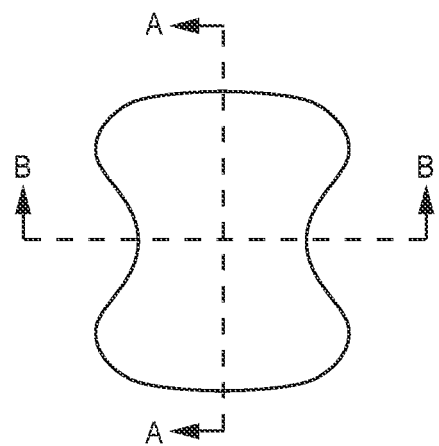
Figure 3C:
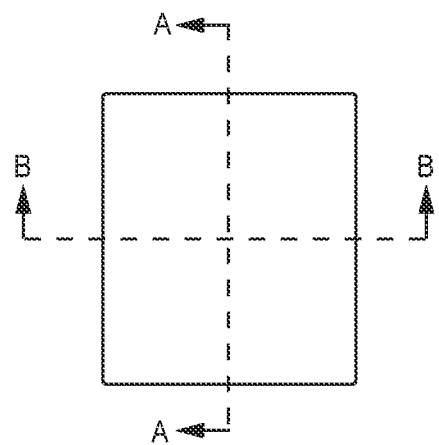
Figure 3D:
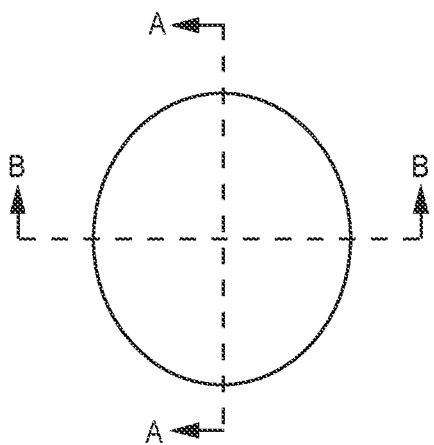

FIGS. 2A-2J depict a preferred embodiment. FIG. 2A is a perspective view of the first back plate. FIG. 2B is a cross-sectional view of the back plate of FIG. 2A taken along line D-D. FIG. 2C is a cross-sectional view of the back plate of FIG. 2A taken along line C-C. FIG. 2D is a top plane view of the back plate of FIG. 2A with the locations of lines C-C and D-D marked. FIG. 2E is a bottom plane view of the back plate of FIG. 2A with the locations of lines C-C and D-D marked. FIG. 2F is a perspective view of the second back plate. FIG. 2G is a cross-sectional view of the back plate of FIG. 2F taken along line F-F. FIG. 2H is a cross-sectional view of the back plate of FIG. 2F taken along line E-E. FIG. 2I is a top plane view of the back plate of FIG. 2F with the locations of lines E-E and F-F marked. FIG. 2J is a bottom plane view of the back plate of FIG. 2F with the locations of lines E-E and F-F marked.

First back plate 901 has first therapeutic sleep surface 903 and second therapeutic sleep surface 905. First therapeutic sleep surface 903 has first convex curve 907 and first concave curve 909. Second therapeutic sleep surface 905 has second convex curve 911 and second concave curve 913. The height of first convex curve 907 is less than the height of second convex curve 911. The depth of first concave curve 909 is less than the depth of second concave curve 913. First back plate 901 has first thickness 915, first width 917, and first length 919.

Second back plate 921 has third therapeutic sleep surface 923 and fourth therapeutic sleep surface 925. Third therapeutic sleep surface 923 has third convex curve 927 and third concave curve 929. Fourth therapeutic sleep surface 925 has fourth convex curve 951 and fourth concave curve 933. The height of second convex curve 911 is less than the height of third convex curve 927. The depth of second concave curve 913 is less than the depth of third concave curve 929. The height of third convex curve 927 is less than the height of fourth convex curve 951. The depth of third concave curve 929 is less than the depth of fourth concave curve 933. Second back plate 921 has second thickness 935, second width 937, and second length 939.

First back plate 901 has first thickness 915 which is the distance between the first therapeutic sleep surface 903 and the second therapeutic sleep surface 905. First back plate 901 has first length 919 which is the distance between first end 908 of first back plate 901 and second end 910 of first back plate 901. First back plate 901 has first width 917 measured from first edge 904 of first back plate 901 and second edge 906 of first back plate 901. First thickness 915 of first back plate 901 is different when taken at different points on first back plate 901. However, first thickness 915 of first back plate 901 is the same when measured along first width 917 of first back plate 901.

Second back plate 921 has second thickness 935 which is the distance between third therapeutic sleep surface 923 and fourth therapeutic sleep surface 925. Second back plate 921 has second length 939 which is the distance between third end 928 of second back plate 921 and fourth end 930 of second back plate 921. Second back plate 921 has second width 937 measured from third edge 924 of second back plate 921 and fourth edge 926 of second back plate 921. Second thickness 935 of second back plate 921 is different when taken at different points on second back plate 921. However, second thickness 935 of second back plate 921 is the same when measured along second width 937 of second back plate 921.

First therapeutic sleep surface 903, second therapeutic sleep surface 905, third therapeutic sleep surface 923, and fourth therapeutic sleep surface 925, are labeled sequentially to indicate the progression of the sleep surfaces. "A" indicates that first therapeutic sleep surface 903 has the least curvature. "D" indicates that fourth therapeutic sleep surface 925 has the greatest curvature. Other sequential indicia may be used, for example numbers, words, or pictographs.

FIGS. 3A-3D depicts top plane views of various alternative shapes for a back plate. The back plate can be shaped in any way that provides sufficient surface area for the patient to sleep on the back plate with the curves aligned properly.

Figure 4A:
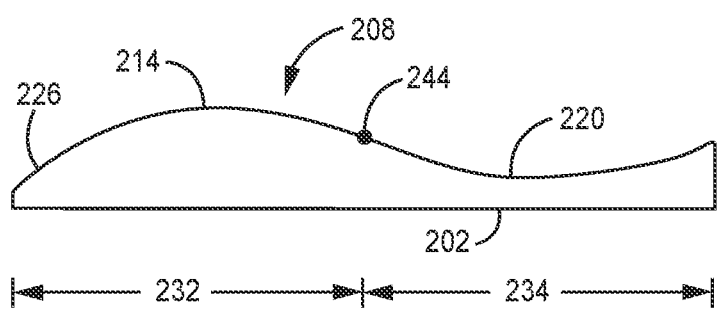
FIGS. 4A-4C is an embodiment of a therapeutic sleep surface system and depict a cross-sectional view taken along lines A-A of any of FIGS. 3A-3D.
Figure 4B:
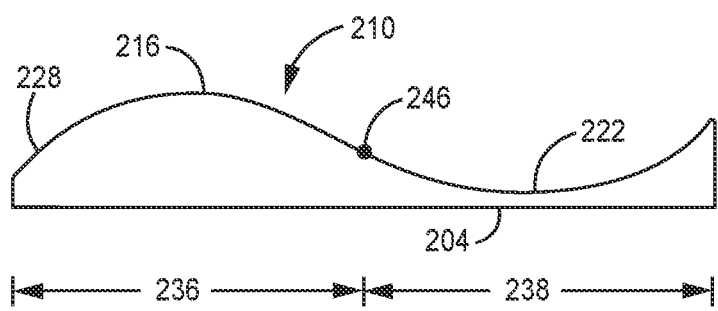
Figure 4C:
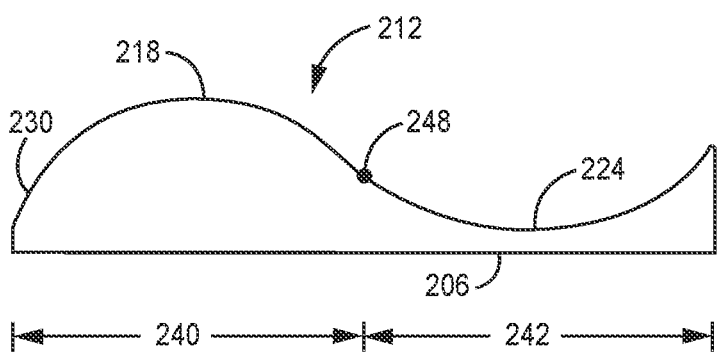

FIGS. 4A-4C shows an embodiment having a series of cross-sectional views through line A-A of back plates for use in a system described herein. Flat bottoms 202, 204, 206 rest on a bed or bed board when in use. Flat bottoms 202, 204, and 206 oppose therapeutic sleep surfaces 226, 228, 230. First back plate 208 should be used first, followed by second back plate 210, and third back plate 212. The height of convex curve 214 is less than the height of convex curve 216. The height of convex curve 216 is less than the height of convex curve 218. The depth of concave curve 220 is less than the depth of concave curve 222. The depth of concave curve 222 is less than the depth of concave curve 224. The lengths of convex curves 232, 236, 240 is the length from inflection point 244, 246, 248 to the edge of the back plates. The lengths of concave curves 234, 238, 242 is the length from inflection point 244, 246, 248 to the edge of the back plates. The curves reverse direction in a continuous manner.

Figure 5A:
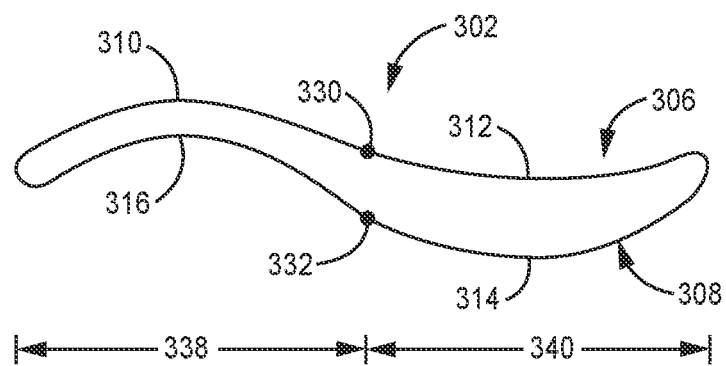
FIGS. 5A-5B is an embodiment of a therapeutic sleep surface system and depict a cross-sectional view taken along lines A-A of any of FIGS. 3A-3D.
Figure 5B:
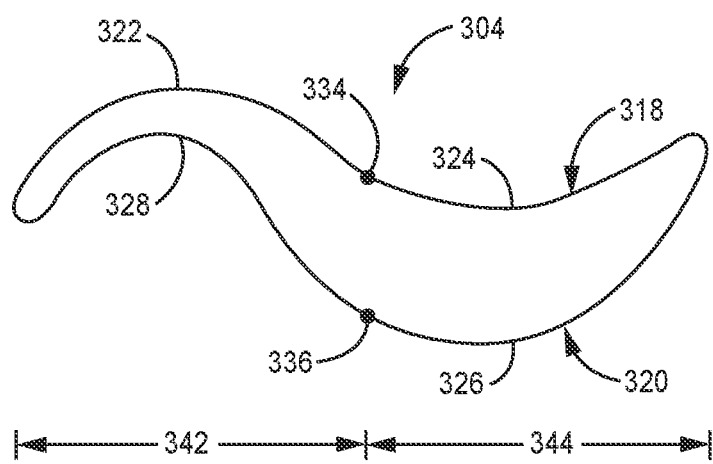
Figure 6A:
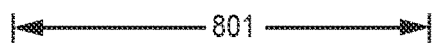
FIGS. 6A-6K are alternative embodiments of a back plate in a cross-sectional views of any of FIGS. 3A-3D taken along lines B-B.
Figure 6B:
Figure 6C:
Figure 6D:
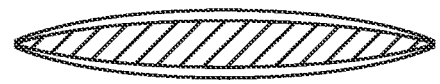
Figure 6E:
Figure 6F:
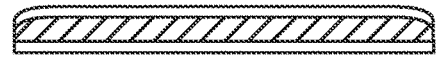
Figure 6G:
Figure 6H:
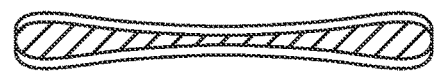
Figure 6I:
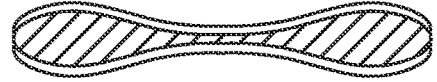
Figure 6J:
Figure 6K:
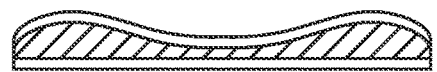

FIGS. 5A and 5B show an embodiment of a back plate system having a series of cross-sectional views through line A-A of back plates for use in a system described herein. First back plate 302 has two therapeutic sleep surfaces, first surface 306 and second surface 308. Second back plate 304 has two therapeutic sleep surfaces, third surface 318 and fourth surface 320. First surface 306, second surface 308, third surface 318 and fourth surface 320 have s-curves. The height of convex curve 310 of the first surface is less than the height of convex curve 314 of the second surface. The height of convex curve 314 of the second surface is less than the height of convex curve 322 of the third surface. The height of the convex curve 322 is less than the height of convex curve 326 of the fourth surface. Similarly, the depth of concave curve 312 of the first surface is less than the depth of concave curve 316 of the second surface. The depth of concave curve 316 of the second surface is less than the depth of concave curve 324 of the third surface. The depth of the concave curve 324 is less than the depth of concave curve 328 of the fourth surface. The length 338 of convex curve 310 is the length from inflection point 330 to the edge of the back plates. The length 340 of convex curve 314 is the length from inflection point 332 to the edge of the back plates. The length 342 of convex curve 322 is the length from inflection point 334 to the edge of the back plates. The length 344 of convex curves 326 is the length from inflection point 336 to the edge of the back plates. The length 340 of concave curve 312 is the length from inflection point 330 to the edge of the back plates. The length 338 of concave curve 316 is the length from inflection point 332 to the edge of the back plates. The length 344 of concave curve 324 is the length from inflection point 334 to the edge of the back plates. The length 342 of concave curves 328 is the length from inflection point 336 to the edge of the back plates.

FIGS. 6A-6K depict various alternate embodiments cross-sectional views through line B-B of back plates for use in a system described herein. Width of back plate 801 extends from one edge of the back plate to the other. In some embodiments there is no curvature along the width of the back plate, for example in FIGS. 6A, 6B, and 6E. In some embodiments a convex or concave curvature may exist along the width of the back plate.

A use of back plates described herein treats mild, moderate, or severe lower back pain at home with or without the prescription or guidance of a physician. Back plates are a firm surface that is placed between the back of the user and a sleeping surface. The back plates are designed to be used in series.

The back plates can be any shape that allows for support of the spine in a wide variety of users. In embodiments the back plates may be square, rectangular, circular, elliptical, or hourglass shapes. The shapes may be long enough to support the lumbar region and sacrum of a user. The length of the back plate is the distance between the edges of the back plate measured along the s-curve. For example the total length of the back plate may be in a range from about 13 inches to about 17 inches, in a range from about 13 inches to about 16 inches, or in a range from about 14 inches to about 15 inches. The length of the back plates may vary between plates in the series. The back plates may be long enough to support additional portions of the spine including the thoracic and cervical spinal regions. The shapes may be wide enough to cover the spinal region as well as some or all of the pelvis. For example, the width of the back plate may be in a range from about 11 inches to about 14 inches, in a range from about 11.5 inches to about 13 inches, or in a range from about 12 inches to about 13 inches. The width of the back plates may vary between plates in the series. The back plate series may come in a variety of sizes to accommodate a wide variety of users based on their height and/or weight, for example small, medium, large. The thickness of the back plate is the distance between the top and bottom surface of a back plate. The thickness of the back plate may be variable. The thickness of a back plate may be in a range from about 0.2 inches to about 5 inches, in a range from about 0.5 inches to about 3 inches, or in a range from about 1 inch to about 2 inches.

Rigid materials are materials that are able to support the spine in the desired position. The back plates may be made of any rigid material. For example, the back plate may be made of plastic, metal, wood, resin, or stiff foam. The material should also be strong enough to support the weight of a user without breaking or significantly deforming. In some embodiments the back plate may flex slightly under the weight of the user. An amount of flex and/or an amount of deformation may be measured by measuring a vertical movement of the rigid surface of the back plate when a user of weight 120-200 pounds rests on the back plate on an immobile surface in a position as intended for use; embodiments include a flex and/or deformation of the rigid surface of the back plate independently selected to be from 0% to 15% or from 0 to 0.5 inches; Artisans will immediately appreciate that all ranges and values between the explicitly stated bounds are contemplated, for example, 0, 1, 2, 3, 4, 5, 10%, or 15% and/or 0, 0.1, 0.2, 0.3, 0.4, and 0.5 inches. Further, a rigid back plate surface may be covered for comfort. For example, the rigid back plate surface may be covered in foam, fabric, batting, and/or a material that comprises a gel.

A back plate series has a number of therapeutic sleep surfaces. A therapeutic sleep surface is a rigid unitary surface comprising a first concave curve and a first convex curve that are joined at an inflection point and reverse direction in a continuous manner, for example as in FIGS. 1, 3, and 4-7. Each back plate in the series has at least one therapeutic sleep surface. In some embodiments each back plate has one therapeutic sleep surface and a flat bottom opposite the therapeutic sleep surface. In some embodiments each back plate has two therapeutic sleep surfaces. The sleep surfaces are opposite each other. The back plates may have flat sides. In other embodiments the back plates may have rounded or cambered sides. The back plate series has a plurality of therapeutic sleep surfaces. For example, the back plate series may have 2, 3, 4, or 5 therapeutic sleep surfaces. The back plate series may have one or more back plates. For example, the back plate series may have 1, 2, 3, or 4 back plates. If the back plate has a flat bottom it may be attached to a bed board.

The first convex curve of the therapeutic sleep surfaces support the lumbar region. The therapeutic sleep surfaces may, and preferably do, further have a concave curve to support the sacrum. Other curves may be present to support additional sections of the spine, for example a further concave curve to support the thoracic region and/or a further convex curve to support the cervical region. The height and depth of the curves are designed to incrementally increase until reaching the natural curvature of a healthy adult. The height of the convex curve may be constant across the width of the rigid unitary surface. The depth of the concave curve may be constant across the width of the rigid unitary surface.

The height of the convex curve is constant in a cross-section taken along a width of a back plate. The depth of the concave curve is constant in a cross-section taken along a width of a back plate. This feature is in contrast to a shape wherein a curve has a dimension of a height or a width that is greater at a center of a back plate and varies to a smaller dimension across a width of the back plate.

The curvature of a healthy spine falls into a standard range in all humans. Differentiation from this normal curvature can cause pain or other health issues. Curvature of the spine is measured through the Cobb Method or the tangential radiological assessment of lumbar lordosis (TRALL). The cervical region has a normal curvature of 20 to 40 degrees. The thoracic region has a normal curvature of 20 to 40 degrees. The lumbar region has a normal curvature 40 to 60 degrees. The convex curve of the back plate can have a curvature in a range from 40 to 60 degrees. The first back plate in the series will have the shallowest curvature. The curvature of the convex curve for the first therapeutic sleep surface may be in a range from about 35% to about 45%. The final back plate in the series will have the deepest curvature. The curvature of the convex curve for the final therapeutic sleep surface may be in a range from about 55% to about 60%. Any therapeutic sleep surfaces used between the first therapeutic sleep surface and the final therapeutic sleep surface will have a curvature that is greater than the first therapeutic sleep surface and less than the final therapeutic sleep surface, for example, in a range from about 40% to about 50%, in a range from about 45% to about 55%, or in a range from about 50% to about 55%. The height of the convex curve for the first therapeutic sleep surface is the shallowest of the sleep surfaces. The height of the convex curve for the final therapeutic sleep surface is the highest of the sleep surfaces. The height of the convex curve of the therapeutic sleep surfaces in between will fall between the height of the first therapeutic sleep surface and the height of the final therapeutic sleep surface. For example, the height of the convex curve of the first therapeutic sleep surface may be in a range from about 0.1 inches to about 0.2 inches, in a range from about 0.1 inches to about 0.17 inches, or in a range from about 0.11 to about 0.15 inches. The height of the convex curve of the intermediate therapeutic sleep surfaces may be in a range from about 0.1 inches to about 0.25 inches, in a range from about 0.12 inches to about 0.21 inches, or bet in a range from about 0.12 to about 0.2 inches. The height of the convex curve of the final therapeutic sleep surface may be in a range from about 0.15 inches to about 0.25 inches, in a range from about 0.17 inches to about 0.25 inches, or in a range from about 0.19 to about 0.23 inches. The depth of the concave curve for the first therapeutic sleep surface is the shallowest of the sleep surfaces. The depth of the concave curve for the final therapeutic sleep surface is the deepest of the sleep surfaces. The depth of the concave curve of the intermediate therapeutic sleep surfaces fall between the depth of the first therapeutic sleep surface and the depth of the final therapeutic sleep surface. For example, the depth of the concave curve of the first therapeutic sleep surface may be in a range from about 0.1 inches to about 0.2 inches, in a range from about 0.1 inches to about 0.17 inches, or in a range from about 0.11 to about 0.15 inches. The depth of the concave curve of the intermediate therapeutic sleep surfaces may be in a range from about 0.1 inches to about 0.25 inches, in a range from about 0.12 inches to about 0.21 inches, or in a range from about 0.12 to about 0.2 inches. The depth of the concave curve of the final therapeutic sleep surface may be in a range from about 0.15 inches to about 0.25 inches, in a range from about 0.17 inches to about 0.25 inches, or in a range from about 0.19 to about 0.23 inches.

The concave and convex curve lengths may differ between the therapeutic sleep surfaces. In some embodiments the inflection points may or may not be vertically aligned between two therapeutic sleep surfaces. The concave curve length and convex curve lengths may or may not be the same. The concave curve length may be in a range from about 5 inches to about 8 inches, in a range from about 5.5 inches to about 7.5 inches, or in a range from about 6 to about 7 inches. The convex curve length may be in a range from about 5 inches to about 8 inches, in a range from about 5.5 inches to about 7.5 inches, or in a range from about 6 and about 7 inches. If a back plate has two therapeutic sleep surfaces, the curves may be nested, as shown in FIG. 4A-B, or they may be in opposition.

OPERATION

Figure 7:
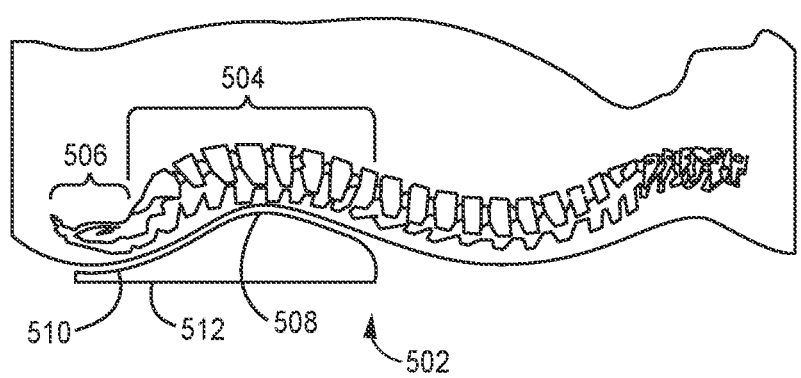
FIG. 7 depicts a cross-sectional view of a back plate in use with the spine of a user.

FIG. 7 depicts back plate 502 in use supporting the spine of a patient. Lumbar region 504 is supported by convex curve 508. Sacrum 506 is supported by concave curve 510. Flat surface 512 is placed on the sleeping surface.

Figure 8:
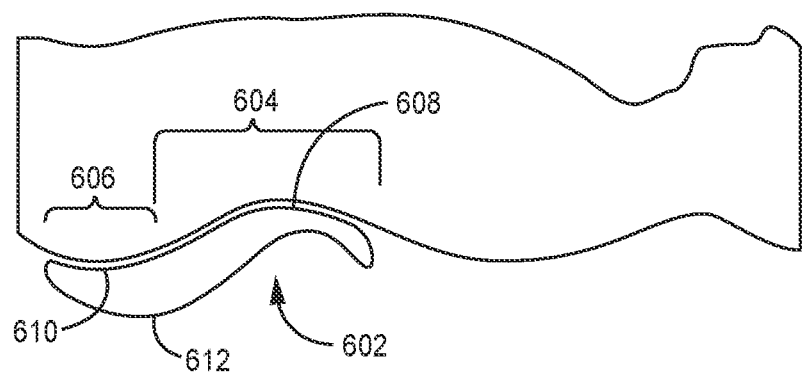
FIG. 8 depicts a cross-sectional view of a back plate in use with the spine of a user.

FIG. 8 depicts back plate 602 in use supporting the spine of a patient. Lumbar region 604 is supported by convex curve 608. Sacrum 606 is supported by concave curve 610. Second curved surface 612 is placed on the sleeping surface.

Figure 9A:
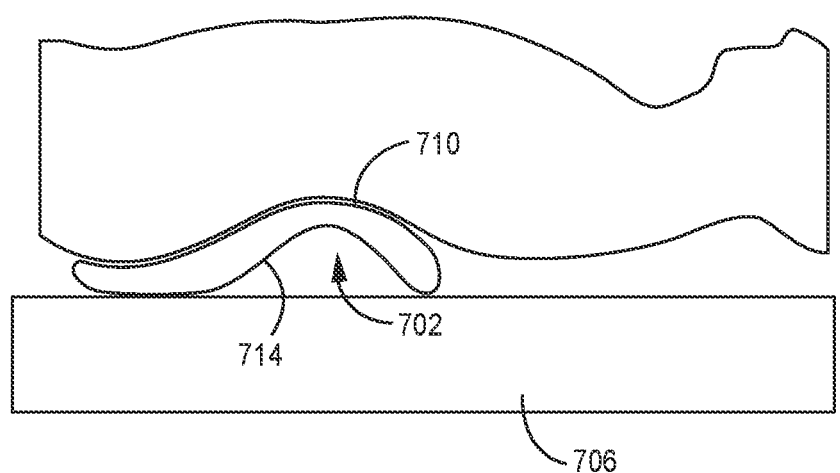
FIG. 9A-9B depicts a cross-sectional elevation view of a back plate in use with a bed or backboard.
Figure 9B:
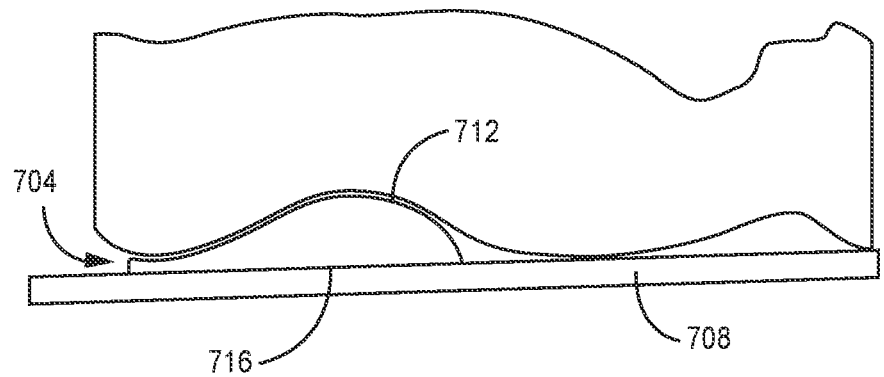

FIGS. 9A and 9B are back plates 702, 704 in use on a bed or bed board 706, 708. The second surface of the back plate 714, 716 is rested on the bed or bed board 706, 708. The first surface of the back plate 710, 712 is oriented toward the patient. The patient then lays on the back plate 710, 712 with the spine supported as indicated in FIGS. 5 and 6.

When the system is used a patient will sleep on the first surface for a first period of time. The patient will then turn the first back plate over and sleep on the second surface for a second period of time. The patient will then sleep on the second back plate on the third surface for a third period of time. Finally, the patient will then turn the second back plate over and sleep on the fourth surface for a fourth period of time. The patient may choose to continue sleeping on the fourth surface continuously or periodically indefinitely.

The back plate series is designed to be used to treat back pain at home. The back plates may be numbered or otherwise marked with an indication of the order that the therapeutic sleep surfaces should be used in.

A user places a back plate on a sleeping surface, for example a bed or backboard, with the desired therapeutic sleep surface facing toward the user. The user lays on the back plate with the convex curve supporting the lumbar region and the concave surface supporting the sacrum. The user then remains in a supine position for the treatment period. The treatment period may be for example 15 minutes, a half hour, an hour, two hours, or overnight. In some embodiments the user may sleep on the back plate. The treatment period may be repeated regularly, defining a frequency. For example the frequency may be every day, every other day, or once a week for a period of time. The period of time may be, for example one week, one month, three months, six months, a year, or more.

The back plate series is used as described, beginning with the therapeutic sleep surface with the shortest convex curve height and concave curve depth. The user switches to the next therapeutic sleep surface in the series after a period of time. This is repeated until the therapeutic sleep surface with the greatest convex curve height and concave curve depth is being used. The individual therapeutic sleep surfaces may be slept on for a period of time, for example, a day, a week, a month, or longer before switching to the next sleep surface. The therapeutic sleep surfaces may be used for the same period of time or a different period time before switching therapeutic sleep surfaces. Use of the back plates may continue for as long as the user or the user's medical professional deems them useful or necessary.

A person of ordinary skill in the art will recognize that additional ranges are contemplated and are within the present disclosure. People of ordinary skill in the art will immediately appreciate that all values and ranges within the expressly stated ranges are contemplated, and are within the present disclosure.

The embodiments above are intended to be illustrative and not limiting. Additional embodiments are within the claims. In addition, although the present invention has been described with reference to particular embodiments, those skilled in the art will recognize that changes can be made in form and detail without departing from the spirit and scope of the invention. Any incorporation by reference of documents above is limited such that no subject matter is incorporated that is contrary to the explicit disclosure herein.

The invention claimed is:

1. A back treatment system for recovery of lumbar vertebrae of a human body, the back treatment system comprising:
    a first back plate having a first rigid unitary surface comprising a first concave curve and a first convex curve that are joined at an inflection point and reverse direction in a continuous manner; and
    a second rigid unitary surface comprising a second concave curve and a second convex curve that are joined at an inflection point and reverse direction in a continuous manner, with the second rigid unitary surface being disposed on a side of the first back plate that is opposite to the first rigid unitary surface or being disposed on a second back plate,
    wherein a height of the second convex curve is greater than a height of the first convex curve.

2. The system of claim 1 wherein the system further comprises a third rigid unitary surface comprising a third concave curve and a third convex curve that are joined at an inflection point and reverse direction in a continuous manner, with the third rigid unitary support surface being disposed on a second back plate or being disposed on a third back plate, and
    a fourth rigid unitary surface comprising a fourth concave curve and a fourth convex curve that are joined at an inflection point and reverse direction in a continuous manner, with the fourth rigid unitary surface being disposed on a second back plate, being disposed on a third back plate, or being disposed on a fourth back plate
    wherein a height of the of the third convex curve is greater than the height of the second convex curve and a height of the fourth convex curve is greater than the height of the third convex curve.

3. The system of claim 2 further comprising a second back plate comprising two surfaces wherein one of the surfaces is a rigid unitary surface.

4. The system of claim 3 wherein the second rigid unitary surface is disposed on the first back plate, the third rigid unitary surface is disposed on the second back plate, and the fourth rigid unitary surface is disposed on the second back plate.

5. The system of claim 1 wherein the first back plate comprises the first rigid unitary surface and the second rigid unitary surface, with the first rigid unitary surface and the second rigid unitary surface being joined by a thickness.

6. The system of claim 5 wherein the thickness is in a range from 0.5 to 3 inches.

7. The system of claim 5 wherein the first or second back plate comprises plastic, metal, wood, or stiff foam.

8. The system of claim 5 wherein the first or second back plate further comprises a covering.

9. The system of claim 1 wherein the height of the first convex curve is in a range from 0.1 inches to 0.17 inches.

10. The system of claim 1 wherein the height of the second convex curve is in a range from 0.17 inches to 0.25 inches.

11. The system of claim 1 wherein the first concave curve has a depth in a range from 0.1 inches to 0.17 inches.

12. The system of claim 1 wherein the second concave curve has a depth in a range from 0.17 inches to 0.25 inches.

13. The system of claim 1 wherein the first rigid unitary surface has a length in a range from about 13 inches to about 17 inches.

14. The system of claim 1 wherein the first rigid unitary surface has a width in a range from 11 inches to 14 inches.

15. The system of claim 1 wherein the first or second rigid unitary surface comprises a label to indicate an order in which a height of the first or second convex curve increases.

16. A method for using the system of claim 1, the method comprising:
  laying on the first rigid unitary surface with the first convex curve under a lumbar region for a first period of time,
  after the first period of time laying on the first rigid unitary surface, laying on the second rigid unitary surface with the second convex curve under the lumbar region.

17. The method of claim 16 further comprising after a second period of time laying on the second rigid unitary surface, laying on a third rigid unitary surface comprising a third convex curve, wherein the third convex curve is placed under the lumbar region, and
wherein a height of the third convex curve is greater than the height of the second convex curve.

18. The method of claim 17 further comprising after a third period of time laying on the third rigid unitary surface, laying on a fourth rigid unitary surface having a fourth convex curve, wherein the fourth convex curve is placed under the lumbar region, and
wherein a height of the fourth convex curve is greater than the height of the third convex curve.

19. The method of claim 16 wherein a user lays on the first rigid unitary surface nightly.

20. A method for using a back treatment system, the method comprising:
  providing the system of claim 1 to a user, and labeling each rigid unitary surface to indicate an order in which a height of the convex curve increases.

* * * * *